United States Patent
Zhang et al.

(10) Patent No.: US 10,933,028 B2
(45) Date of Patent: Mar. 2, 2021

(54) METHOD OF PREPARING PH/REDUCTION RESPONSIVE POLYAMINO ACID ZWITTERIONIC NANOPARTICLES

(71) Applicant: JIANGNAN UNIVERSITY, Jiangsu (CN)

(72) Inventors: Liping Zhang, Jiangsu (CN); Caihua Ni, Jiangsu (CN); Ren Liu, Jiangsu (CN); Dawei Wang, Jiangsu (CN); Gang Shi, Jiangsu (CN); Xinxin Sang, Jiangsu (CN); Xiaofeng Xia, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 16/494,993

(22) PCT Filed: Dec. 3, 2018

(86) PCT No.: PCT/CN2018/118862
§ 371 (c)(1),
(2) Date: Sep. 17, 2019

(87) PCT Pub. No.: WO2019/214219
PCT Pub. Date: Nov. 14, 2019

(65) Prior Publication Data
US 2020/0281865 A1 Sep. 10, 2020

(30) Foreign Application Priority Data
May 8, 2018 (CN) .......................... 201810432125.X

(51) Int. Cl.
*A61K 9/51* (2006.01)
*A61K 31/337* (2006.01)
*A61K 31/351* (2006.01)

(52) U.S. Cl.
CPC .......... *A61K 9/5192* (2013.01); *A61K 9/5146* (2013.01); *A61K 31/337* (2013.01); *A61K 31/351* (2013.01)

(58) Field of Classification Search
CPC .. A61K 9/5146; A61K 9/5192; A61K 31/337; A61K 31/351
See application file for complete search history.

(56) References Cited

U.S. PATENT DOCUMENTS

2004/0151774 A1* 8/2004 Pauletti ................ A61K 31/337
424/486

FOREIGN PATENT DOCUMENTS

| CN | 102875733 A | 1/2013 |
|---|---|---|
| CN | 103976949 A | 8/2014 |
| CN | 104491871 A | 4/2015 |
| CN | 105001442 A | 10/2015 |
| CN | 105820334 A * | 8/2016 |
| CN | 108498483 A | 9/2018 |

OTHER PUBLICATIONS

Evariso Pegion et al. "Polymerization of gamma-Benzyl-L-Glutamate N-Carboxy-anhydride: Effects of Conditions of Polymer Precipitation on the Molecular Weight Distribution" in BIOPOLYMERS, vol. 4, oo. 695-704 (1966).*
Liping Zhang, Luyan Wu, Gang Shi, Xinxin Sang & Caihua Ni, Studies on the preparation and controlled release of redox/pH-responsive zwitterionic nanoparticles based on poly-L-glutamic acid and cystamine [J]. Journal of Biomaterials Science, Polymer Edition. 2018, 29, 646-662.
LuyanWu, Liping Zhang, Gang Shi, Caihua Ni. Zwitterionic pH/redox nanoparticles based on dextran as drug carriers for enhancing tumor intercellular uptake of doxorubicin [J]. Materials Science and Engineering C, 2016, 61, 278-285.
Luyan Wu, Caihua Ni, Liping Zhang & Gang Shi. Preparation of pH-sensitive zwitterionic nano micelles and drug controlled release for enhancing cellular uptake [J]. Journal of Biomaterials Science, Polymer Edition. 2016, 27 (7), 643-656.
Yuanyuan Ding, Liping Zhang, Gang Shi, Xinxin Sang, Caihua Ni. Preparations and doxorubicin controlled release of amino-acid based redox/pH dual-responsive nanomicelles [J]. Materials Science and Engineering C, 77 (2017) 920-926.
International Search Report dated Jan. 24, 2019 for related PCT/CN2018/118862 filed Dec. 3, 2018.

* cited by examiner

*Primary Examiner* — Blessing M Fubara
(74) *Attorney, Agent, or Firm* — Enshan Hong; VLP Law Group LLP

(57) ABSTRACT

The invention discloses a preparation method of pH/reduction responsive polyamino acid zwitterionic nanoparticles, which belongs to the technical field of polymer synthesis and biomedical materials. In the invention aliphatic amines are used to initiate ring-opening polymerization of γ-benzyl-L-glutamate-N-carboxylic anhydride, and the obtained poly (γ-benzyl-L-glutamate) reacts with L-lysine to form azwitterionic polymer. The zwitterionic polymer is crosslinked by cysteamine, producing pH/reduction responsive polyamino acid zwitterionic nanoparticles after purification. The nanoparticles are pH responsive and resistant to non-specific protein adsorption. Because cysteamine contains disulfide bonds, the nanoparticles have sensitive reductive responsiveness and can load anticancer drugs for controlled release at the target site of cancer.

9 Claims, 2 Drawing Sheets

METHOD OF PREPARING PH/REDUCTION RESPONSIVE POLYAMINO ACID ZWITTERIONIC NANOPARTICLES

RELATED APPLICATIONS

This is a U.S. national stage of international application No. PCT/CN2018/118862 filed on Dec. 3, 2018, which claims priority from China Patent Application No. 201810432125X filed on May 8, 2018, the entire content of which is incorporated herein as reference.

1. TECHNICAL FIELD

The invention relates to a method of preparing pH/reduction responsive polyamino acid zwitterionic nanoparticles, which belongs to the technical fields of polymer synthesis and biomedical materials.

2. BACKGROUND ART

Cancer is believed to be the leading cause of death. Chemotherapy is an important method to treat cancer at present, but it not only kills cancer cells, but also has great toxic and side effects on normal cells. Anti-cancer drugs are easy to be cleared by reticuloendothelial system, resulting in poor cell absorption. The nano-drug carrier system can enhance the permeability and retention (EPR) effect, avoid the recognition and capture of human reticular endocortical system, prolong the circulation time of drug delivery system in the blood, and improve the bioavailability of drugs.

Zwitterionic ionic polymers have high abilities of hydration and bacterial adhesion resistance, can resist non-specific protein adsorption, effectively avoid macrophage uptake, achieve the "invisible" function in the blood circulation system; they can also change charge reversible and can be chemically modified, so they are expected to become excellent substitutes for polyethylene glycol. At present, most of the zwitterionic ionic polymers reported in the literature are non-biodegradable. This will lead to a series of problems, such as incomplete release of drugs and adverse side effects caused by the residual part of polymer degradation. Another problem is that the existing zwitterionic polymers have no pH/reductive responsiveness, which makes it difficult to control drug release at the tumor site.

The pH and reductive environment of tumor cells are special. Tumor cells are slightly acidic. The concentration of glutathione in tumor cells is 100 to 1000 times higher than that in body fluids or other tissues. It has a strong reductive effect on disulfide bonds. Therefore, the design of environmentally responsive drug carriers, using the pH and reductive environment of tumor sites for drug-controlled release, has become an effective method.

Polyglutamic acid is a biodegradable polymer with good biocompatibility. Poly (L-glutamic acid) and its derivatives degrade slowly in vivo. As drug carriers, polyglutamic acid can prolong the drug circulation time in vivo and contribute to the sustained release and targeted drug delivery. The side chains of polyglutamic acid contain carboxyl groups, which can react with amino groups.

L-Lysine is one of the essential amino acids for human body, and it is often used in the preparation of drug carriers. The amino groups of lysine can react with carboxyl groups of side chains of polyglutamic acid, to form zwitterionic ions. The reported methods for preparing nanoparticles based on L-lysine are complex and time-consuming, and the prepared polyamino acid are only acid-sensitive but have no reduction responsiveness as drug carriers.

It has been reported that natural polyglutamic acid can be directly cross-linked with cysteamine to synthesize nano microgels. However, natural products have wide distribution of molecular weight and impurities, and the size of nanoparticles is not easy to control. Moreover, the rate of direct amination of carboxyl and amino groups is slow, and the degree of reaction is difficult to control.

SUMMARY OF THE INVENTION

To solve these problems, the aim of the present invention is to provide a preparation method of pH/reduction responsive polyamino acid zwitterionic nanoparticles. First, the main chain of polyglutamic acid is synthesized by ring-opening polymerization, then L-lysine is introduced into the side chain through a group reaction to form zwitterionic ions, and finally, nanoparticles are formed by a cross-linking reaction. The nanoparticles have anti-nonspecific protein adsorption ability and are pH responsive due to the existence of zwitterionic ions. The nanoparticles are also reduction sensitive since disulfide bonds are involved in the crosslinking structure. Anticancer drugs can be loaded in the nanoparticles and be controlled for release at the target site of tumor cells.

The first object of the invention is to provide a preparation method of pH/reduction responsive polyamino acid zwitterionic nanoparticles, comprising the following steps:

Step 1: Ring-opening polymerization of γ-benzyl-L-glutamate-N-carboxylic anhydride is initiated by an aliphatic amine and performed, giving poly(γ-benzyl-L-glutamate);

Step 2: A zwitterionic polymer is formed by a reaction of L-lysine with the poly(γ-benzyl-L-glutamate);

Step 3: The zwitterionic polymer is crosslinked with cysteamine and is purified to obtain pH/reduction responsive polyamino acid zwitterionic nanoparticles.

In one embodiment of the present invention, in step 1), the aliphatic amine is one of n-pentamine, n-hexamine, n-heptamine, n-octylamine, cyclopentamine, cyclohexylamine or benzylamin.

In one embodiment of the present invention, in step 1), dichloromethane, chloroform or 1,2-dichloroethane is used as a solvent.

In one embodiment of the present invention, in step 1), the molar ratio of initiator to γ-benzyl-L-glutamate-N-carboxylic anhydride is 1:25-30.

In one embodiment of the present invention, in step 2), the molar ratio of L-lysine to γ-benzyl-L-glutamate-N-carboxylic anhydride is 0.5~0.8:1.

In one embodiment of the present invention, in step 1), the ring-opening polymerization is carried out at 20-30° C. for 15-24 hours under protection of nitrogen.

In one embodiment of the present invention, in step 1), the ring-opening polymerization is carried out at 20-30° C. for 15-24 hours under protection of nitrogen.

In one embodiment of the present invention, in step 2), the reaction temperature is 20-30° C. for 10-15 hours.

In one embodiment of the present invention, in step 3), the cross-linking of zwitterionic polymer by cysteamine includes the following steps: cysteamine hydrochloride solution containing an acid binding agent is added to the zwitterionic polymer, and the reaction is carried out at 20-40° C. for 10-15 hours under stirring, then ultrapure water is added by dropping into the obtained reaction solution until nanoparticles appear, and nanoparticle solution is dialyzed for 40-60 hours to obtain pH/reductive responsive polyamino acid zwitterionic nanoparticles.

In one embodiment of the present invention, in step (3): the molar ratio of cysteamine hydrochloride to zwitterionic polymers is 0.25~0.1:1.

In one embodiment of the present invention, in step (3): the acid binding agent is triethylamine, and the molar number of acid binding agent is 1-3 times related to cysteamine hydrochloride.

In one embodiment of the present invention, in Step 1, the aliphatic amine is dissolved in dichloromethane, and γ-benzyl-L-glutamate-N-carboxylic anhydride in dichloromethane solution is added. An ring-opening polymerization of γ-benzyl-L-glutamate-N-carboxylic anhydride initiated by the aliphatic amine is carried out at 20-30° C. for 15-24 hours under the protection of nitrogen. The product of the reaction is precipitated with anhydrous petroleum ether and the product is washed with water several times. The intermediate product of poly(γ-benzyl-L-glutamate) was obtained by vacuum drying at 20-30° C. for 40-50 h at the constant temperature.

In one embodiment of the invention, the concentration of γ-benzyl-L-glutamate-N-carboxylic anhydride in dichloromethane solution is 16-20 w %.

In one embodiment of the present invention, in step 2, the intermediate product obtained in step 1 is dissolved in tetrahydrofuran, mixed with L-lysine, stirred for 10-15 hours at 20-30° C., precipitated with anhydrous petroleum ether, and dried at 20-30° C. in vacuum to obtain zwitterionic polymer.

In one embodiment of the present invention, in step 3, the zwitterionic polymer obtained in step 2 is dissolved in the solution of N, N-dimethylformamide, cysteamine hydrochloride and triethylamine are added, and the reaction is carried out at 20-40° C. for 10-15 hours under stirring. Ultrapure water is added to the solution under magnetic stirring until the nanoparticles appear. The solution is transferred to the dialysis bag for dialysis 40-60 hours, and the pH/reductive responsive polyamino acid zwitterionic nanoparticles are obtained after freeze-drying.

The second object of the present invention is to provide the method for preparing the pH/reduction responsive polyamino acid zwitterionic nanoparticles The third object of the invention is to provide an application of the pH/reduction responsive polyamino acid zwitterionic nanoparticles in the preparation of drug carriers. In the application a drug is dissolve in N, N-dimethylformamide, then the prepared pH/reduction responsive polyamino acid zwitterionic nanoparticles are placed in the above-mentioned drug solution under stirring, after dialysis and freeze-dry the drug-loaded nanoparticles are obtained.

In one embodiment of the invention, the drug is doxorubcin or paclitaxel.

The advantages of the invention are:

1. In the first step, poly(γ-benzyl-L-glutamate) is prepared by ring-opening polymerization of γ-benzyl-L-glutamate-N-carboxylic anhydride initiated by an aliphatic amine. The reaction is easy, the structure of the product is regular, the molecular weight and the nanoparticles size are controllable.

2. In the second step of the invention, L-lysine is introduced into the side chain through a substitution reaction. The reaction is irreversible, and the conversion rate of the group can be controlled by feeding ratio, so that the product performance can be more controllable. The reaction is simple, and the operation is easy.

3. In the ring-opening polymerization hydrophobic aliphatic amine is introduced, which is beneficial for self-assembly of the polymers in aqueous solution and to form nanoparticles.

4. All the raw materials have good biocompatibility, no cytotoxicity, no harm to human body, and the products have application prospects.

5. The disulfide bond in cysteamine is introduced into the cross-linking structure, which makes the nanoparticles reduction sensitive; the zwitterionic ion structure of L-lysine makes the nanoparticles pH-responsive. It is conducive for loading anticancer drugs and controlling the release at the target site of cancer.

DESCRIPTION OF PREFERRED EMBODIMENTS

Figure 1:
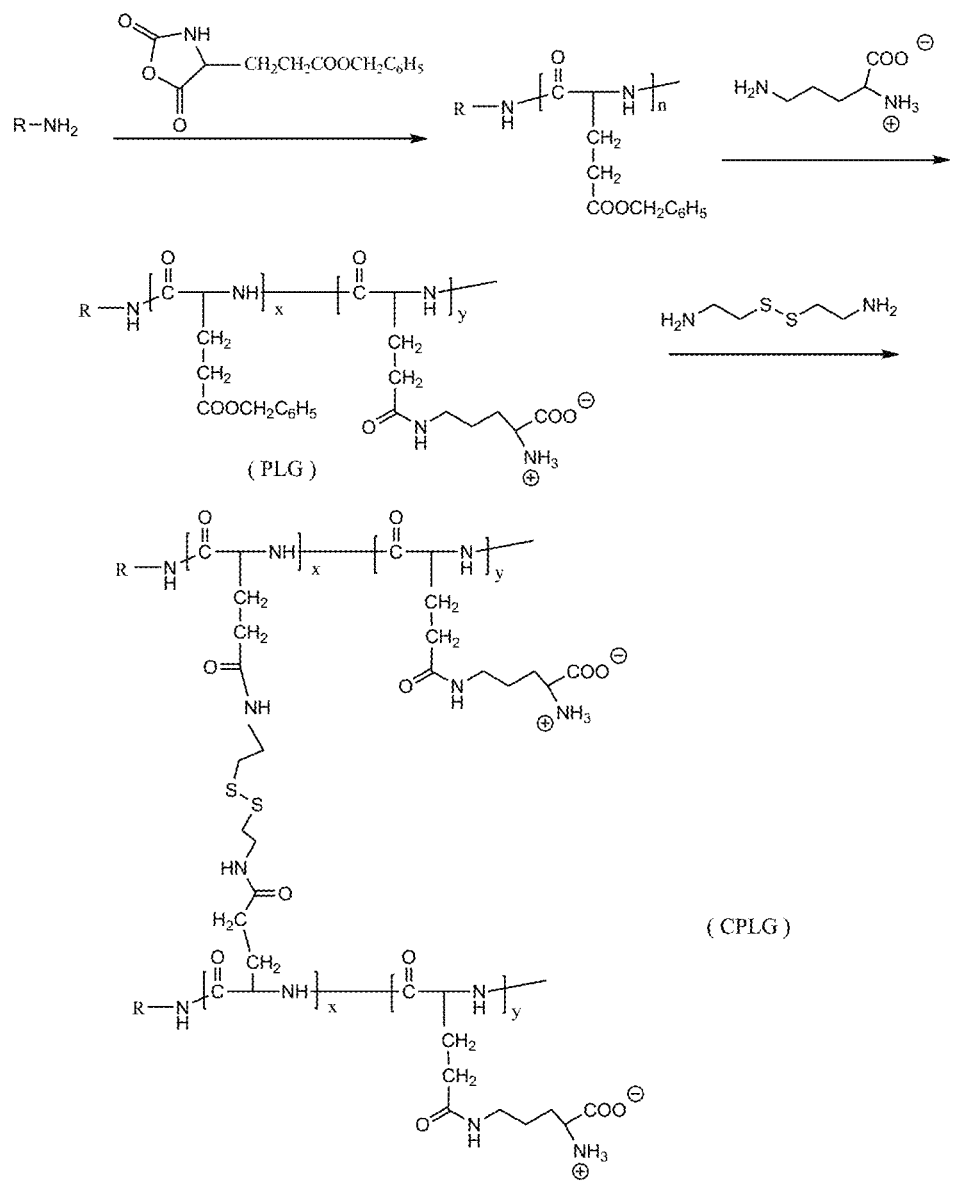
FIG. 1 Preparation scheme of the pH/reduction responsive polyamino acid zwitterionic nanoparticles in the invention.

The detailed implementation of the invention is further described as follows. The following embodiments are used to illustrate the invention, but not to limit the scope of the invention.

Example 1

Monomer Preparation:

In a 500 mL flask 80 g of L-glutamic acid and 65 g of benzyl alcohol were added, the mixture was heated up to 70° C. slowly under magnetic stirring, and 86 g of 50 w % of sulfuric acid dropwise added for a reaction. After vacuum distillation, the reaction liquid was poured into $NaHCO_3$ solution until neutralization. The mixture was cooled at 4° C., static and vacuum filtrated. The product was washed with ethanol and distilled water for three times, and then recrystallizing in 5% ethanol solution at 70° C. The crystals were cooled at 4° C. for overnight, and finally dried in vacuum at 35° C. for 48 hours to obtain white flaky solid, which was γ-benzyl-L-glutamate. The above γ-benzyl-L-glutamate 12.2 g was added into a three-necked flask containing 120 mL tetrahydrofuran and heated to 40° C. in water bath to dissolve the γ-benzyl-L-glutamate. Triphosgene 17.0 g was added to the reaction solution. A transparent solution was obtained after a reaction for 5 hours under the protection of nitrogen. HCl gas and residual phosgene produced by the reaction were continuously driven by nitrogen gas. The reaction liquid was slowly dripped into excessive petroleum ether and cooled by ice bath. The white acicular crystals were separated through a vacuum filtration and purified by tetrahydrofuran/anhydrous petroleum ether. The γ-benzyl-L-glutamate-N-carboxylic anhydride was obtained after vacuum drying at 35° C.

Ring-opening polymerization: The n-heptamine 0.383 g was dissolved in dichloromethane 40 g in a three-necked flask; a solution of 26.3 g the γ-benzyl-L-glutamate-N-carboxylic anhydride in 80 g dichloromethane was slowly added to the above n-heptamine solution, stirred for 20 hours at 25° C. under the protection of nitrogen, a ring-opening polymerization of γ-benzyl-L-glutamate-N-carboxylic anhydride initiated by n-heptamine took place. The polymerization product was precipitated by petroleum ether, and washed with deionized water for several times, the intermediate product of poly(γ-benzyl-L-glutamate) was obtained after drying in vacuum state at 25° C. for 48 hours.

Substitution reaction in side chains: The obtained poly(γ-benzyl-L-glutamate) was dissolved in 100 ml tetrahydrofuran, 7.3 g L-lysine was added, and stirred for 12 hours at 25° C. The partially substituted product in side chains was precipitated with petroleum ether, separated and dried at 25° C. in vacuum state. The product was labeled as PLG.

Crosslinking reaction: The above PLG was dissolved in 120 ml N, N-dimethylformamide, then 5.63 g cysteamine hydrochloride and 5.1 g triethylamine were added, stirred for 12 hours at 30° C. Ultra-pure water was dripped into the solution under magnetic stirring until nanoparticles appeared. The nanoparticle solution was transferred into a dialysis bag for dialysis for 48 hours. The pH/reduction responsive polyamino acid zwitterionic nanoparticles were obtained after freeze-drying. The sample was labeled as CPLG-1 in Table 1.

Example 2

As in example 1, sample CPLG-2 was synthesized by changing the weight of L-lysine to 8.76 g and remaining other steps unchanged.

Example 3

As in example 1, sample CPLG-3 was synthesized by changing the weight of L-lysine to 10.22 g and remaining other steps unchanged.

Example 4

As in example 1, sample CPLG-4 was synthesized by changing the weight of L-lysine to 11.68 g and remaining other steps unchanged.

Example 5

As in example 1, but the weight of γ-benzyl-L-glutamate-N-carboxylic anhydride was changed to 21.9 g, L-lysine was 8.03 g, cysteamine hydrochloride was 5.60 g, and triethylamine was 5.07 g, and remaining other steps unchanged. The sample was labeled as CPLG-5 in Table 1.

Example 6

As in example 1, but the weight of cysteamine hydrochloride was changed to 2.25 g, and remaining other steps unchanged. The sample was labeled as CPLG-6 in table 1.

TABLE 1 preparation of pH/reduction responsive polyamino acid zwitterionic nanoparticles

| Sample ID | n-heptamine (g) | γ-benzyl-L-glutamate-N-carboxylic anhydride (g) | L-lysine (g) | cysteamine hydrochloride (g) | triethylamine (g) |
|---|---|---|---|---|---|
| CPLG-1 | 0.383 | 26.3 (0.10 moL) | 7.30 (0.05 moL) | 5.63 | 5.10 |
| CPLG-2 | 0.383 | 26.3 (0.10 moL) | 8.76 (0.06 moL) | 5.63 | 5.10 |
| CPLG-3 | 0.383 | 26.3 (0.10 moL) | 10.22 (0.07 moL) | 5.63 | 5.10 |
| CPLG-4 | 0.383 | 26.3 (0.10 moL) | 11.68 (0.08 moL) | 5.63 | 5.10 |
| CPLG-5 | 0.383 | 21.9 (0.083 moL) | 8.03 (0.055 moL) | 5.60 | 5.07 |
| CPLG-6 | 0.383 | 26.3 (0.10 moL) | 7.30 (0.05 moL) | 2.25 | 5.10 |

Example 7

The dried drug-loaded nanoparticles were placed in ultra-pure water to prepare an aqueous solution (concentration 0.15 mg/mL). The pH of the nanoparticle solution was adjusted using 0.1 M NaOH and 0.1 M HCl solution. The hydration particle size and zeta potential of drug-loaded nanoparticles were measured under different pHs at 25° C. The results were shown in Table 2.

TABLE 2

Characterizations and properties of the nanoparticles

| Sample ID | Hydration particle size (nm) | | | Zeta potential (mV) | | | Lp (%) | |
|---|---|---|---|---|---|---|---|---|
| | pH 4 | pH 7.4 | pH 9 | pH 4 | pH 7.4 | pH 9 | Doxorubicin | Paclitaxel |
| CPLG-1 | 250 | 120 | 309 | 10 | −5 | −20 | 10.2 | 8.6 |
| CPLG-2 | 255 | 124 | 298 | 11 | −7 | −22 | 11.5 | 8.9 |
| CPLG-3 | 259 | 130 | 307 | 12 | −6.5 | −25 | 12.8 | 9.6 |
| CPLG-4 | 260 | 129 | 312 | 15 | −8 | −32 | 13.2 | 10.5 |
| CPLG-5 | 261 | 125 | 318 | 11 | −6 | −21 | 12.0 | 9.8 |
| CPLG-6 | 280 | 135 | 350 | 12 | −8 | −23 | 8.2 | 7.8 |

Example 8

Firstly, the anti-cancer drug doxorubicin or paclitaxel was dissolved in N, N-dimethylformamide to form a solution with a concentration of 2 mg/mL; then the nanoparticles were prepared based on claims 1-8; the 50 mg nanoparticles were dissolved in 5 mL of the above anti-cancer solution, after stirring for 24 hours, the solution was transferred to dialysis bags for dialysis 12 hours, the drug-loaded nanoparticles were obtained after freeze-drying.

The dried drug-loaded nanoparticles 10 mg were dissolved in N, N-dimethyl formamide 10 mL. The absorbance of doxorubicin was measured at 483 nm by ultraviolet spectrophotometer. Using the standard curve, the drug loading percentage (Lp) was determined. The calculation formula was as follows:

$$Lp\ (\%) = (W_L/W_N) \times 100$$

Where $W_L$ was weight of drug loaded, and $W_N$ was weight of dried nanoparticles; the results were shown in Table 2.

Example 9

Figure 2:
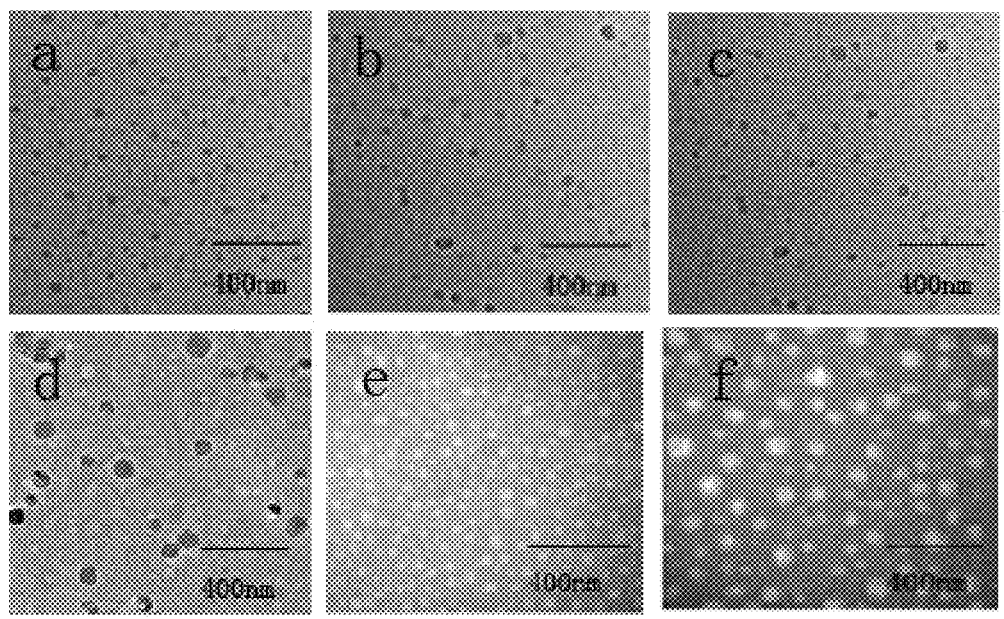
FIG. 2 Photos of transmission electron microscopy (TEM) of the pH/reduction responsive polyamino acid zwitterionic nanoparticles, a: CPLG-1; b: CPLG-2; c: CPLG-3; d: CPLG-4; e: CPLG-5; f: CPLG-6.

Transmission electron microscopy (TEM) image of nanoparticles: 20 uL of nanoparticles solution was dripped onto the copper mesh, then a drop of 1.0 wt % phosphotungstic acid solution was added to dye the nanoparticles. The copper mesh was dried naturally at room temperature. The morphology of nanoparticles prepared by different formulations was observed by TEM. The acceleration voltage was 120 kV. The results were shown in FIG. 2.

Example 10

Reduction sensitivity: Firstly, pyrene acetone solution (0.5 mg/L) was prepared, then the solution 100 μL was added to 10 mL of the nanoparticle solution (0.1 mg/mL) in a container. Glutathione was added to the container after 1 the acetone was completely volatilized, and the concentration of glutathione was 10 mM.

Figure 3:
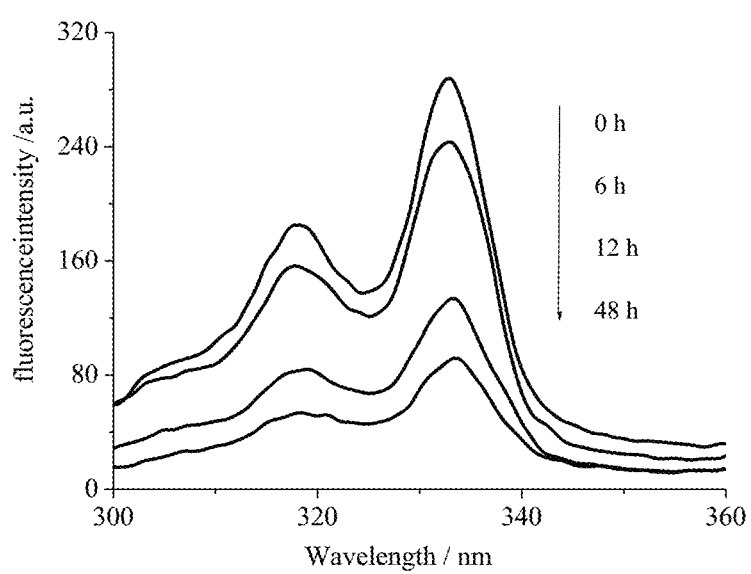
FIG. 3 Fluorescence emission spectra of pyrene solubilized nanoparticles CPLG-1 incubated in 10 mM glutathione (GSH) solution at 37° C.

The solution was incubated at 37 C. The fluorescence spectra of the solution at different time were determined by fluorescence spectrophotometer as shown in FIG. 3. The emission wavelength was set at 395 nm and the slit width was set at 5 cm. Pyrene is a hydrophobic molecule which can be solubilized in nanoparticles. Once the hydrophobic environment is destroyed, pyrene will leak into water, causing changes in its fluorescence intensity.

The above description was only a preferred implementation method of the invention and is not used to limit the invention. Some improvements and variations based on the invention should also be considered as the scope of protection of the invention.

What is claimed is:

1. A method of preparing pH/reduction responsive polyamino acid zwitterionic nanoparticles comprising the following steps:
    step (1): in a three-necked flask an aliphatic amine is dissolved in dichloromethane, then γ-benzyl-L-glutamate-N-carboxylic anhydride in dichloromethane solution is slowly added under stirring, a ring opening polymerization is carried out to obtain an intermediate product, the intermediate product is precipitated by anhydrous petroleum ether, washed for several times with deionized water, and is dried in vacuum, poly(γ-benzyl-L-glutamate) is obtained;
    step (2): the obtained poly(γ-benzyl-L-glutamate) is dissolved in tetrahydrofuran, L-lysine is added, the substitution reaction is carried out under stirring, the reaction product is precipitated with anhydrous petroleum ether, dried in vacuum to form zwitterionic polymers;
    step (3): the above-mentioned zwitterionic polymer is crosslinked with cysteamine to obtain the pH/reduction responsive polyamino acid zwitterionic nanoparticles, wherein in step (1): the aliphatic amine is one of n-pentamine, n-hexamine, n-heptamine, n-octylamine, cyclopentamine or cyclohexylamine.

2. The method of claim 1 wherein in step (2): the molar number of L-lysine is 50%-80% related to γ-benzyl-L-glutamate-N-carboxylic anhydride.

3. The method of claim 1 wherein in step (1): the ring-opening polymerization is carried out at 20-30° C. for 15-24 hours under protection of nitrogen.

4. The method of claim 1 wherein in step (2): the reaction temperature is 20-30° C., and the reaction time is 10-15 hours.

5. The method of claim 1 wherein in step (3): the zwitterionic polymer is crosslinked by cysteamine, includes: cysteamine hydrochloride solution containing acid-binding agent is added to the zwitterionic polymer solution and reacted at 20-40° C. for 10-15 hours under stirring, then ultrapure water is added by dropping into the obtained solution until nanoparticles appear, and nanoparticle solution is dialyzed for 40-60 hours to obtain pH/reductive responsive polyamino acid zwitterionic nanoparticles.

6. The method of claim 5 wherein the molar number of cysteamine hydrochloride is 10%~25% related to zwitterionic polymers.

7. The method of claim 5 wherein the acid-binding agent is triethylamine, and the molar number of acid-binding agent is 1-3 times related to cysteamine hydrochloride.

8. PH/reduction responsive polyamino acid zwitterionic nanoparticles prepared by the method described in claim 1.

9. A method of making drug-loaded nanoparticles comprising: firstly an anti-cancer drug doxorubicin or paclitaxel is dissolved in N, N-dimethylformamide to form an anti-cancer solution; then the nanoparticles are prepared based on claim 1; the nanoparticles are dissolved in the anti-cancer solution, after stirring for 24 hours, the solution is transferred to dialysis bags for dialysis, therefore obtaining the drug-loaded nanoparticles after freeze-drying.

* * * * *